(12) United States Patent
Luo et al.

(10) Patent No.: US 8,183,425 B2
(45) Date of Patent: May 22, 2012

(54) IONIC LIQUID CATALYST ALKYLATION USING SPLIT REACTANT STREAMS

(75) Inventors: Huping Luo, Richmond, CA (US); Abdenour Kemoun, Pleasant Hill, CA (US); Hye-Kyung Timken, Albany, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 669 days.

(21) Appl. No.: 12/003,580

(22) Filed: Dec. 28, 2007

(65) Prior Publication Data

US 2009/0171134 A1    Jul. 2, 2009

(51) Int. Cl.
*C07C 2/58* (2006.01)

(52) U.S. Cl. ........ 585/714; 585/720; 585/721; 585/727; 585/728; 585/729; 585/926

(58) Field of Classification Search .................. 585/714, 585/721, 723, 728, 729, 730, 720, 727, 926
See application file for complete search history.

(56) References Cited

U.S. PATENT DOCUMENTS

| | | | | |
|---|---|---|---|---|
| 3,696,168 A | * | 10/1972 | Vanderveen | 585/720 |
| 4,094,923 A | * | 6/1978 | Dixon | 585/714 |
| 4,225,742 A | * | 9/1980 | Hutson, Jr. | 585/723 |
| 5,345,027 A | * | 9/1994 | Child et al. | 585/720 |
| 5,347,064 A | | 9/1994 | Child et al. | |
| 5,750,455 A | | 5/1998 | Chauvin et al. | |
| 6,028,024 A | | 2/2000 | Hirschauer et al. | |
| 6,288,281 B1 | | 9/2001 | Nemeth et al. | |
| 6,743,962 B2 | | 6/2004 | O'Rear et al. | |
| 7,256,152 B2 | | 8/2007 | Olivier-Bourbigou et al. | |
| 2003/0060359 A1 | | 3/2003 | Olivier-Bourbigou et al. | |
| 2003/0158457 A1 | * | 8/2003 | Gershuni | 585/719 |
| 2004/0077914 A1 | | 4/2004 | Zavilla et al. | |
| 2004/0204622 A1 | * | 10/2004 | Smith et al. | 585/731 |
| 2006/0129014 A1 | * | 6/2006 | Gray et al. | 585/709 |
| 2006/0131209 A1 | | 6/2006 | Timken et al. | |
| 2006/0135839 A1 | * | 6/2006 | Elomari et al. | 585/721 |

OTHER PUBLICATIONS

James Gary and Glenn Handwerk Petroleum Refining—Technology and Economics, Third Edition ExxonMobile auto refrigeration alkylation process published at p. 243.
Roebuck, A,.K. And Evering, B.L., "Isobutane-Olefin Alkylation with Inhibited Aluminum Chloride Catalysts" Ind. Eng. Chem,. Prod. Res. Develop., publ. , vol. 9, pp. 76-82 (1970).
U.S. Appl. No. 12/003,574, filed Dec. 28, 2007 for "Ionic Liquid Catalyzed Alkylation Process Employing Nozzles and system Implementing Such Process" inventors Luo et al.
U.S. Appl. No. 12/003,576, filed Dec. 28, 2007 for "Ionic Liquid Catalyst Alkylation Using a Loop Reactor", inventors Luo et al.
International Preliminary Report and Written Opinion from PCT/US2008/084114, mailed Jul. 8, 2010, 6 pages.

* cited by examiner

*Primary Examiner* — In Suk Bullock
*Assistant Examiner* — Bradley Etherton
(74) *Attorney, Agent, or Firm* — Merchant & Gould

(57) ABSTRACT

Provided is a process for producing low volatility, high quality gasoline blending components from a number of isoparaffin feed streams, olefin feed streams, and ionic liquid catalyst streams. The process entails providing an isoparaffin feed stream comprising isoparaffins, an olefin feed stream comprising olefins, and a catalyst stream comprising ionic liquid catalyst, and subsequently splitting at least the reactive olefin feed stream for feeding into the reaction zone at different locations.

16 Claims, 4 Drawing Sheets

Note: $(I/O)_0$ stands for Overall I/O ratio in total feed

IONIC LIQUID CATALYST ALKYLATION USING SPLIT REACTANT STREAMS

FIELD OF ART

The present invention relates to a more efficient process for producing low volatility, high quality gasoline blending components by using split reactant streams. More specifically, the present invention relates to a process for producing low volatility, high quality gasoline blending components wherein alkylation between isoparaffins and olefins in the presence of an ionic liquid catalyst occurs at high effective I/O ratio (Isoparaffin/Olefin), achieved by splitting reactant streams.

BACKGROUND

Modern refineries employ many upgrading units such as fluid catalytic cracking (FCC), hydrocracking (HCR), alkylation, and paraffin isomerization. As a result, these refineries produce a significant amount of isopentane. Historically, isopentane was a desirable blending component for gasoline having a high octane (92 RON), although it exhibited high volatility (20.4 Reid vapor pressure (RVP)). As environmental laws began to place more stringent restrictions on gasoline volatility, the use of isopentane in gasoline was limited because of its high volatility. As a consequence, the problem of finding uses for by-product isopentane became serious, especially during the hot summer season. Moreover, as more gasoline compositions contain ethanol instead of MTBE as their oxygenate component, more isopentane had to be kept out of the gasoline pool in order to meet the gasoline volatility specification. So, the gasoline volatility issue became even more serious, further limiting the usefulness of isopentane as a gasoline blending component.

An alkylation process, which is disclosed in U.S. Patent Application Publication 2006/0131209, was developed that is capable of converting the undesirable, excess isopentane into desirable and much more valuable low-RVP gasoline blending components. The contents of U.S. Patent Application Publication 2006/0131209 are incorporated by reference herein. This alkylation process involves contacting isoparaffins, preferably isopentane, with olefins, preferably ethylene, in the presence of an ionic liquid catalyst to produce the low-RVP gasoline blending components. This process eliminates the need to store or otherwise use isopentane and eliminates concerns associated with such storage and usage. Furthermore, the ionic liquid catalyst can also be used with conventional alkylation feed components (e.g. isobutane, propylene, butene, and pentene).

The ionic liquid catalyst distinguishes this novel alkylation process from conventional processes for converting light paraffins and light olefins to more lucrative products. Conventional processes include the alkylation of paraffins with olefins, and polymerization of olefins. For example, one of the most extensively used processes in the field is the alkylation of isobutane with $C_3$-$C_5$ olefins to make gasoline cuts with high octane number. However, this and all conventional processes employ sulfuric acid and hydrofluoric acid catalysts.

Numerous disadvantages are associated with sulfuric acid and hydrofluoric acid catalysts. Extremely large amounts of acid are necessary to initially fill the reactor. The sulfuric acid plant also requires a huge amount of daily withdrawl of spent acid for off-site regeneration. Then the spent sulfuric acid must be incinerated to recover $SO_2$/$SO_3$ and fresh acid is prepared. While an HF alkylation plant has on-site regeneration capability and daily make-up of HF is orders of magnitude less, HF forms aerosol. Aerosol formation presents a potentially significant environmental risk and makes the HF alkylation process less safe than the $H_2SO_4$ alkylation process. Modern HF processes often require additional safety measures such as water spray and catalyst additive for aerosol reduction to minimize the potential hazards. The ionic liquid catalyst alkylation process fulfills the need for safer and more environmentally-friendly catalyst systems.

Benefits of the ionic liquid catalyst alkylation process include the following:

(1) substantial reduction in capital expenditure as compared to sulfuric acid and hydrofluoric acid alkylation plants;

(2) substantial reduction in operating expenditures as compared to sulfuric acid alkylation plants;

(3) substantial reduction in catalyst inventory volume (potentially by 90%);

(4) a substantially reduced catalyst make-up rate (potentially by 98% compared to sulfuric acid plants);

(5) a higher gasoline yield;

(6) comparable or better product quality (Octane number, RVP, T50);

(7) significant environment, health and safety advantages;

(8) expansion of alkylation feeds to include isopentane and ethylene; and (9) higher activity and selectivity of the catalyst.

Ionic liquid catalysts specifically useful in the alkylation process described in U.S. Patent Application Publication 2006/0131209 are disclosed in U.S. Patent Application Publication 2006/0135839, which is also incorporated by reference herein. Such catalysts are chloroaluminate liquid catalysts comprising an alkyl substituted pyridium halide or an alkyl substituted imidazolium halide of the general formulas A and B, respectively. Such catalysts further include chloroaluminate liquid catalysts comprising a hydrocarbyl substituted pyridium halide or an hydrocarbyl substituted imidazolium halide of the general formulas A and B, respectively.

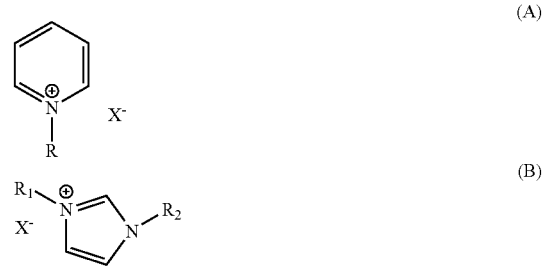

where R=H, methyl, ethyl, propyl, butyl, pentyl or hexyl group and X is a halide and preferably a chloride, and $R_1$ and $R_2$=H, methyl, ethyl, propyl, butyl, pentyl, or hexyl group and where $R_1$ and $R_2$ may or may not be the same. Preferred catalysts include 1-butyl-4-methyl-pyridinium chloroaluminate (BMP), 1-butyl-pyridinium chloroaluminate (BP), 1-butyl-3-methyl-imidazolium chloroaluminate (BMIM) and 1-H-pyridinium chloroaluminate (HP).

However, the ionic liquid catalyst has unique properties, which requires that the ionic liquid catalyst alkylation process be further developed and modified to achieve superior gasoline blending component products, improved process operability and reliability, reduced operating costs, etc. More particularly, the ionic liquid catalyst alkylation process requires uniform mixing of the hydrocarbons and catalyst, sufficient interfacial contact between the hydrocarbons and catalyst, good temperature and pressure control, and a high isoparaffin to olefin (I/O) ratio. In addition, alkylation by means of the ionic liquid catalyst is an exothermic reaction requiring the removal of heat generated.

An alkylation process disclosed in U.S. Pat. No. 5,347,064 (Child et al.) and an ExxonMobil auto refrigeration alkylation process published at page 243 of the third edition of *Petroleum Refining—Technology and Economics* by James Gary and Glenn Handwerk offer some attempts at improvements in general alkylation reactions, although the reactions are sulfuric acid alkylations.

The Child et al. process separates an olefin feed stream comprising at least three olefins into intermediate streams enriched in propene, 1-butene, and 2-butenes, respectively. Then a first intermediate stream enriched in propene contacts at least one isoparaffin (e.g. isobutane) in a first reaction zone at a reaction temperature specific to propene to produce a first alkylate product, a second intermediate stream enriched in 1-butene contacts the at least one isoparaffin in a second reaction zone at a reaction temperature specific to 1-butene to produce a second alkylate product, and a third intermediate stream enriched in 2-butenes contacts the at least one isoparaffin in a third reaction zone at a reaction temperature specific to 2-butenes to produce a third alkylate product. Segregation of the olefin components prior to alkylation improves alkylate quality by increasing the ratio of triemethylpentanes to dimethylhexanes in the alkylate product.

The ExxonMobil process mixes an olefin feed and a recycled isobutane stream to form a combined stream and then divides the combined stream into several streams that enter a continuous-stirred tank reactor at various points along the horizontal length of the reactor. The acid used to catalyze the reaction between the olefin feed and isobutane enters the reactor at one point only.

While the Child et al. and ExxonMobil process result in certain benefits, there still exists a need for an improved alkylation process for converting isoparaffins and olefins in the presence of an ionic liquid catalyst.

SUMMARY

Provided is a process for producing low volatility, high quality gasoline blending components from a number of isoparaffin feed streams, olefin feed streams, and ionic liquid catalyst streams. It entails providing an isoparaffin feed stream comprising isoparaffins, an olefin feed stream comprising olefins, and a catalyst stream comprising ionic liquid catalyst and subsequently splitting at least the reactive olefin feed stream for feed into the reaction zone, or splitting all the feed streams into a plurality of isoparaffin feed streams, olefin feed streams, and catalyst streams. The splitting of at least the olefin feed stream and introducing the split feed streams at separate entry points into the reaction zone allows for better control of the reaction.

Among other factors, it has been discovered that by splitting at least the most reactive hydrocarbon reactant, i.e., the olefin, and introducing the split feed streams at separate points in the reaction zone, a higher effective isoparaffin/olefin (I/O) ratio can be achieved and controlled. A higher I/O ratio results in better selectivity, as side reactions are minimized, and thus an overall better alkylation reaction is achieved.

DETAILED DESCRIPTION

Figure 1:
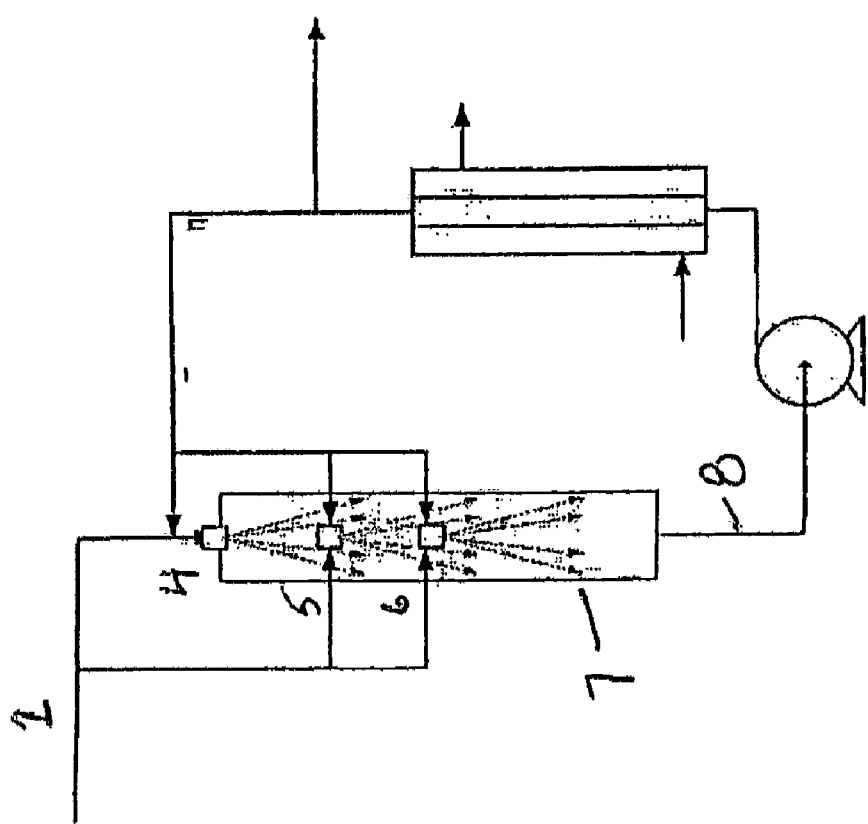
FIG. 1 is a schematic of an embodiment wherein the hydrocarbon feed stream is split and injected at three different injection points.

In one embodiment, there is provided a process for the production of low volatility, high quality gasoline blending components by means of alkylation of isoparaffins with olefins in the presence of an ionic liquid catalyst. The process involves providing three feed streams: (1) an isoparaffin feed stream comprising isoparaffins; (2) an olefin feed stream comprising olefins; and (3) a catalyst stream comprising an ionic liquid catalyst. The process further involves splitting the feed streams into a plurality of feed streams, and introducing the split feed streams into a reactor at different injection points. In one embodiment, at least the olefin feed stream is split and injected at different introduction points into the reactor. The process is further illustrated in the Figures of the Drawing.

Referring to FIG. 1, a process is depicted which uses an external loop for recirculating a stream and multiple injection points into the reactor for the hydrocarbon feed. The hydrocarbon feeds 1, comprised of an isoparaffin feed and an olefin feed mixed together, is split and injected at three different points, 4, 5 and 6, into the alkylation zone/reactor 7. In one embodiment, the feed streams are injected or fed into the reactor through nozzles. Effluent 8 from the reactor generally comprises isoparaffin, catalyst and reaction product. Essentially all of the olefin is reacted, as the I/O (isoparaffin/olefin) ratio is maintained as high as practical in order to ensure complete reaction. At the beginning of the reaction process the I/O ratio is generally around 10:1 as injected into the reactor 7. However, the effective ratio in the reactor, as the reaction occurs, can be generally 1,000:1, or 10,000:1, or even higher, as almost all of the olefin is reacted and substantially only isoparaffin remains of the reactants.

Figure 2:
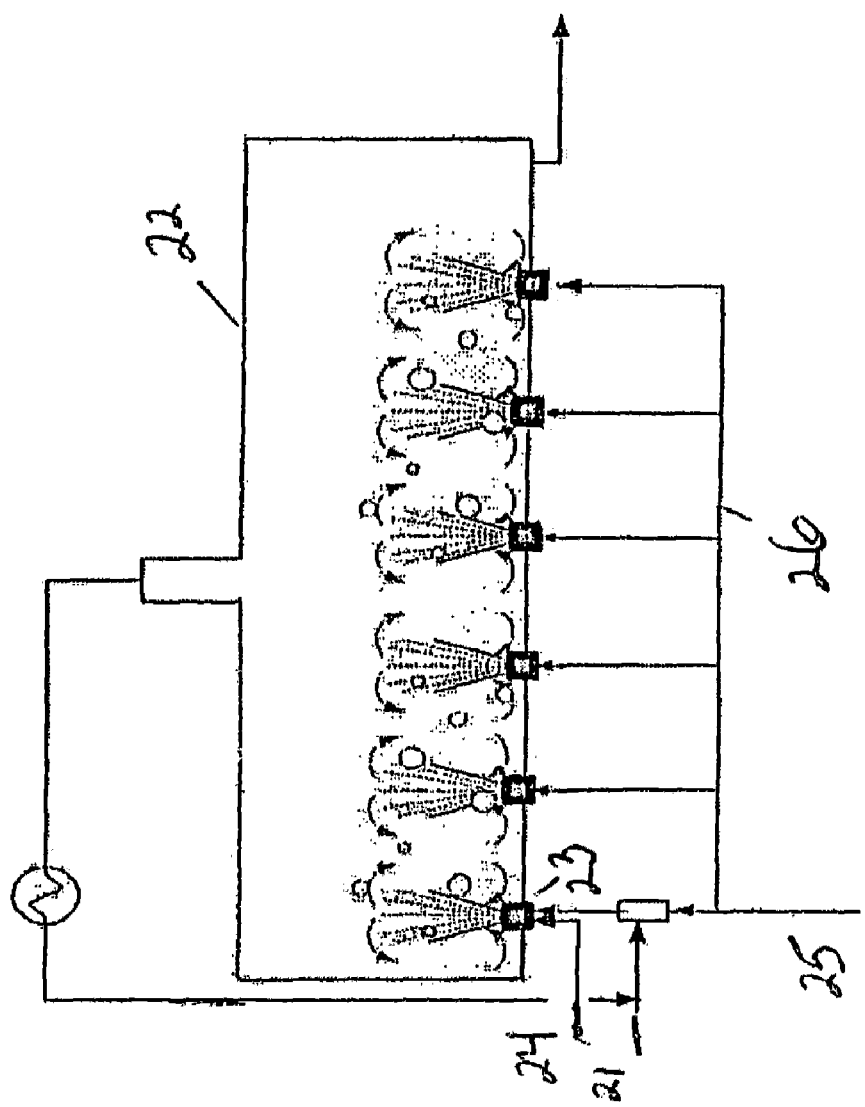
FIG. 2 is a schematic of another embodiment wherein the olefin reactant is split and injected at numerous points into the reactor.

Another embodiment is shown in FIG. 2, using a horizontal reactor. Isoparaffin 21 is injected into the reactor 22 at a first nozzle 23. Catalyst 24 is also injected at nozzle 23. Olefin 25 is injected into the reactor at multiple olefin injection points 26, which increases the internal I/O ratio and provides improved mixing inside the reactor. This same system can be used in a vertical reactor with the catalyst and isoparaffin being injected at the top and the olefin feed at various points along the length of the reactor.

As a result of the multiple injection points of the olefin, the I/O ratio can be controlled and maintained within the reactor at a very high effective level. By maintaining the effective I/O ratio within the reactor at a high level, the alkylation is improved as selectivity is enhanced by avoiding undesirable side reaction.

One of the feedstocks to the present process are refinery streams referred to herein as olefin feed streams, each of which contain olefins. Examples of sources of the olefin feed streams include FCC offgas, coker gas, olefin metathesis unit offgas, polyolefin gasoline unit offgas, methanol to olefin unit offgas, and methyl-t-butyl ether unit offgas. In one embodiment the olefin feed streams comprise ethylene. A source of ethylene for conducting the process is offgas from an FCC unit, which may contain up to about 20 vol % of ethylene. However, other olefins may make up the olefin feed streams.

Examples of such olefins include propylene, butylenes and pentenes. Specifically, the olefins in the olefin feed streams comprise at least one olefin selected from the group consisting of ethylene, propylene, butene, pentene, and mixtures thereof.

Another feedstock to the present invention are refinery streams referred to herein as isoparaffins feed streams, each of which contain isoparaffins. Examples of isoparaffins include isobutane, isopentane, and mixtures thereof. In one embodiment the isoparaffins are isopentane. Refinery streams which contain isopentane and which may be used in the process include, but are not limited to, extracted isopentane from an FCC unit, isopentane from a hydrocracking unit, $C_5$ and $C_6$ streams from crude unit distillation, and extracted $C_5$ and $C_6$ streams from a reformer. If isobutane is included in the isoparaffin feed streams, it may be obtained, for example, from hydrocracking units or may be purchased.

In one embodiment, the olefin feed streams only include ethylene and the isoparaffin feed streams contain isobutane and/or isopentane.

The present process employs an ionic liquid catalyst. A large number of ionic liquid catalysts are known in the art which are capable of effecting alkylation of isoparaffins, such as isobutane or isopentane, by olefins, such as propylene, 1-butene, 2-butene, and isobuylene.

The present process can employ a catalytic composition comprising at least one aluminum halide and at least one quaternary ammonium halide and/or at least one amine halohydrate. An example of an aluminum halide which can be used in accordance with the invention is aluminum chloride. Quaternary ammonium halides which can be used in accordance with the invention are described in U.S. Pat. No. 5,750,455, which is incorporated by reference herein, which also teaches a method for the preparation of the catalyst. An exemplary ionic liquid catalyst is N-butylpyridinium chloroaluminate ($C_5H_5NC_4H_9Al_2Cl_7$).

The ionic liquid catalyst can also be a pyridinium or imidazolium-based chloroaluminate ionic liquid. These ionic liquid have been found to be much more effective in the alkylation of isopentane and isobutane with ethylene that aliphatic ammonium chloroaluminate ionic liquid (such as tributyl-methyl-ammonium chloroaluminate). The ionic liquid catalyst can be a chloroaluminate ionic liquid catalyst comprising a hydrocarbyl substituted pyridinium halide or a hydrocarbyl substituted imidazolium halide. Alternatively, the ionic liquid catalyst can be a chloroaluminate ionic liquid catalyst comprising an alkyl substituted pyridinium halide or an alkyl substituted imidazolium halide. More specifically, the ionic liquid catalyst may selected from the group consisting of:

a chloroaluminate ionic liquid catalyst comprising a hydrocarbyl substituted pyridinium halide mixed in with aluminum trichloride or a hydrocarbyl substituted imidazolium and aluminum trichloride preferably in 1 molar equivalent hydrocarbyl substituted pyridinium halide or hydrocarbyl substituted imidazolium halide to 2 molar equivalents aluminum trichloride of the general formulas A and B, respectively;

a chloroaluminate ionic liquid catalyst comprising an alkyl substituted pyridinium chloride and aluminum trichloride or an alkyl substituted imidazolium chloride and aluminum trichloride preferably in 1 molar alkyl substituted pyridinium chloride or alkyl substituted imidazolium chloride to 2 molar equivalents of aluminum trichloride of the general formulas A and B, respectively;

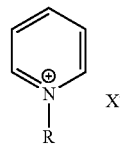
(A)

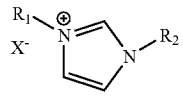
(B)

and mixtures thereof, where R=H, methyl, ethyl, propyl, butyl, pentyl or hexyl group and X is a haloaluminate and preferably a chloroaluminate, and $R_1$ and $R_2$=H, methyl, ethyl, propyl, butyl, pentyl, or hexyl group and where $R_1$ and $R_2$ may or may not be the same.

Preferably the ionic liquid catalyst is selected from the group consisting of 1-butyl-4-methyl-pyridinium chloroaluminate (BMP), 1-butyl-pyridinium chloroaluminate (BP), 1-butyl-3-methyl-imidazolium chloroaluminate (BMIM), 1-H-pyridinium chloroaluminate (HP), and N-butylpyridinium chloroaluminate ($C_5H_5NC_4H_9Al_2Cl_7$).

A metal halide may be employed as a co-catalyst to modify the catalyst activity and selectivity. Commonly used halides for such purposes include NaCl, LiCl, KCl, $BeCl_2$, $CaCl_2$, $BaCl_2$, $SiCl_2$, $MgCl_2$, $PbCl_2$, CuCl, $ZrCl_4$, and AgCl as published by Roebuck and Evering (Ind. Eng. Chem. Prod. Res. Develop., Vol. 9, 77, 1970). Preferred metal halides are CuCl, AgCl, $PbCl_2$, LiCl, and $ZrCl_4$.

HCl or any Broensted acid may be employed as an effective co-catalyst to enhance the activity of the catalyst by boosting the overall acidity of the ionic liquid-based catalyst. The use of such co-catalysts and ionic liquid catalysts that are useful in practicing the present invention are disclosed in U.S. Published Patent Application Nos. 2003/0060359 and 2004/0077914. Other co-catalysts that may be used to enhance the catalytic activity of the ionic liquid catalyst include IVB metal compounds preferably IVB metal halides such as $TiCl_3$, $TiCl_4$, $TiBr_3$, $TiBr_4$, $ZrCl_4$, $ZrBr_4$, $HfCl_4$, and $HfBr_4$ as described by Hirschauer et al. in U.S. Pat. No. 6,028,024.

Due to the low solubility of hydrocarbons in ionic liquids, olefins-isoparaffins alkylation, like most reactions in ionic liquids is generally biphasic and takes place at the interface in the liquid state. The catalytic alkylation reaction is generally carried out in a liquid hydrocarbon phase, in a batch system, a semi-batch system or a continuous system. The molar ratio between the isoparaffin and the olefin is in the range of 1 to 100, for example, advantageously in the range of 2 to 50, preferably in the range 2 to 20. Catalyst volume in the reaction cells is in the range of 2 vol % to 70 vol %, preferably in the range of 5 vol % to 50 vol %. Vigorous mixing is desirable to ensure good contact between the reactants and the catalyst. The reaction temperature can be in the range −40° C. to 150° C., preferably in the range −20° C. to 100° C. The pressure can be in the range from atmospheric pressure to 8000 kPa, preferably sufficient to keep the reactants in the liquid phase. Residence time of reactants in the reaction cells is in the range of a few seconds to hours, preferably 0.5 min to 60 min.

Typical reaction conditions may include a catalyst volume in the reaction cells of 5 vol % to 50 vol %, a temperature of −10° C. to 100° C., a pressure of 300 kPa to 2500 kPa, an isoparaffin to olefin molar ratio of 2 to 10, and a residence time of 1 min to 1 hour.

The following examples are provided to further illustrate the present process and the advantages thereof. The examples are meant to be only illustrative, and not limiting.

EXAMPLES

Example 1

C4 Olefin and Isobutane Alkylation

Evaluation of C4 olefin alkylation with isobutane was performed in a 1000 cc continuously stirred tank reactor. A mixture of isobutane and C4 olefins with varying I/O ratio (molar ratio between isobutane and C4 olefins) was fed to the reactor while vigorously stirring at 1600 RPM. N-butylpyridinium chloroaluminate ($C_5H_5NC_4H_9Al_2Cl_7$) ionic liquid catalyst was purchased and used as received. An ionic liquid catalyst was fed to the reactor via a second inlet port targeting to occupy 5-10 vol % in the reactor. A small amount of anhydrous t-butylchloride was added to the process. The average residence time (combined volume of feeds and catalyst) was about 20 minutes. The outlet pressure was maintained at 150 psig using a backpressure regulator. The reactor temperature was maintained at 15° C. using external cooling. The reactor effluent was separated into multi distillation columns to collect alkylate hydrocarbon phase. Detailed composition of alkylate gasoline was analyzed using gas chromatography.

Figure 3:
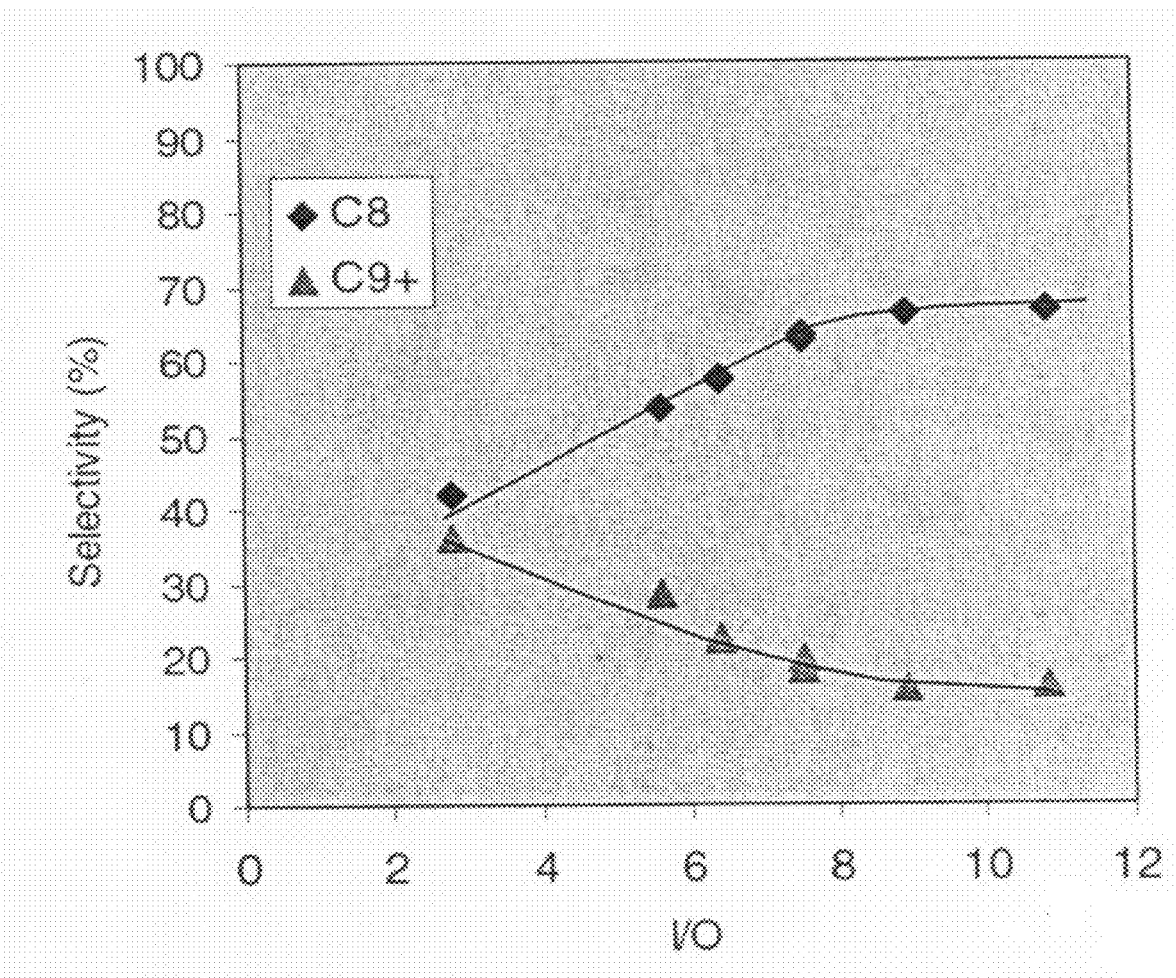
FIG. 3 graphically depicts the effect of I/O ratio on alkylation selectivity.

To study the effect of I/O ratio on reaction selectivity, the I/O ratio in the feedstock was varied from 3 to 11 while keeping all other parameters constant. FIG. 3 shows the profile of alkylation selectivity vs. I/O ratio. It clearly indicates that, as I/O ratio increases, the desired products (i.e., C8 components) increase while the undesired heavy products (i.e., C9+ components) decrease under the studied conditions. As can be seen, such effects are especially prominent at low I/O ratio due to the high olefin concentration, which promotes olefin polymerization and other by-product reactions producing a significant amount of undesired heavy products.

Example 2

Effective I/O Ratio With Multiple Olefin Feed Injections

The primary and desired reactions between isobutane and C4 olefins can be written as:

$$iC4 + C4 = \rightarrow iC8 \quad (1)$$

Each mole of C4 olefin, thus, will consume one mole of isobutane. Due to the importance of high I/O ratio as discussed in Example 1, excessive isobutane is always used in alkylation reactions. The effective I/O ratio inside of a reactor will increase as the olefin is consumed. For example, for a feed mixture with an 8 mole isobutane and 1 mole C4 olefin (i.e., I/O ratio of 8:1), if half of a mole olefin has been consumed, a half mole of isobutane will also be consumed. This results in a mixture with 7.5 moles of isobutane and 0.5 mole of C4 olefin, or an I/O ratio of 15.

Figure 4B:
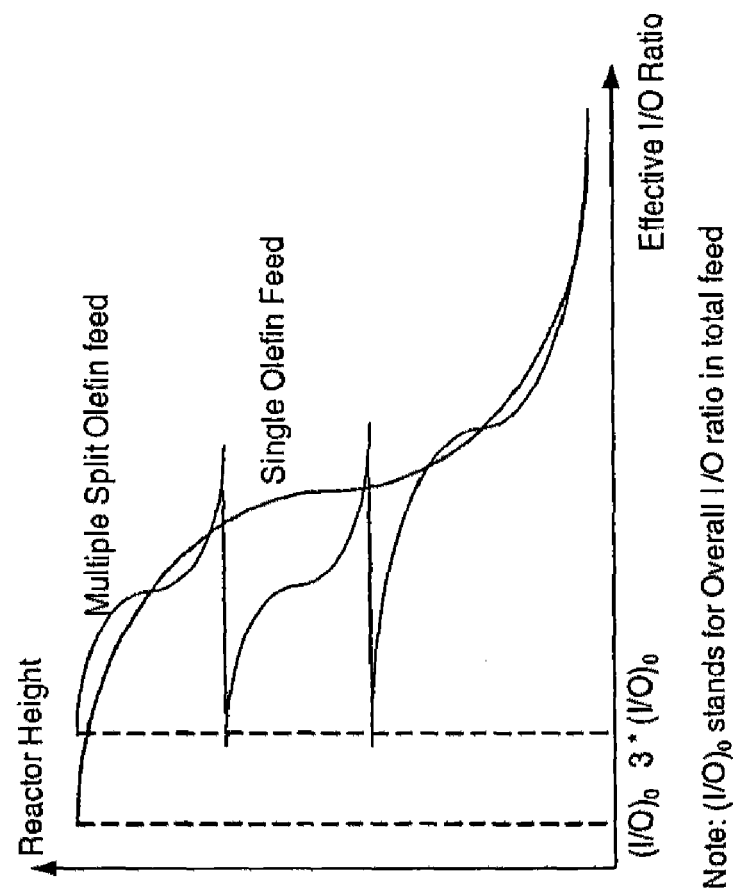
FIGS. 4*a* and 4*b* graphically illustrate and depict the effective I/O ratio along the reactor length when the olefin feed is split and injected at multiple points.
Figure 4A:
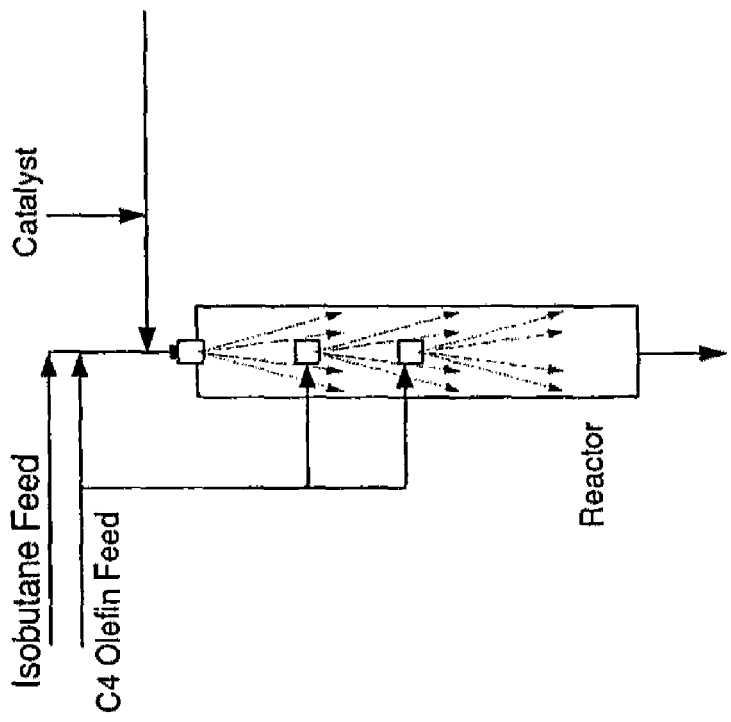

Such an effective I/O ratio can be calculated for a reactor system with known reaction rates. For a reactor system with olefin feed splits into three injections as shown in FIG. 4a, the effective I/O ratio along the reactor length can be illustrated as in FIG. 4b. For comparison, the effective I/O ratio for a reactor system with only one olefin injection is also shown in FIG. 4. As can be seen, with split olefin feeds, the lowest effective I/O ratio is about 3 times higher than the overall I/O ratio in total feed while keeping a high effective I/O ratio throughout the reactor length. This will considerably avoid the higher order by product reactions, such as olefin polymerization, which produce heavy undesired products.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

What is claimed is:

1. A downflow process for the production of low volatility, high quality gasoline blending components comprising:
    (a) providing an isoparaffin feed stream comprising isoparaffins;
    (b) providing an olefin feed stream comprising olefins;
    (c) providing a catalyst stream comprising an ionic liquid catalyst;
    (d) splitting the isoparaffin feed stream, the catalyst stream, and the olefin feed stream into multiple isoparaffin feed streams, catalyst streams, and olefin feed streams;
    (e) feeding the multiple isoparaffin feed streams, catalyst streams, and olefin feed streams into a reactor at different feed sites along the length of the reactor in a downwardly direction to contact all the feed streams under alkylation conditions to provide a product comprising the low volatility, high quality gasoline blending components wherein the isoparaffin/olefin ratio increases along the length of the reactor; and
    (f) isolating the low volatility, high quality gasoline blending components from the product.

2. The process according to claim 1, wherein the reactor is a continuous-stirred tank reactor.

3. The process according to claim 1, wherein the olefin is fed into the reactor at least 3 different sites.

4. The process according to claim 1, wherein the I/O ratio within the reactor is controlled by selecting the number and location of sites for injecting olefin feed into the reactor.

5. The process according to claim 1, wherein the olefins comprise at least one olefin selected from the group consisting of ethylene, propylene, butene, pentene, and mixtures thereof.

6. The process according to claim 1, wherein the isoparaffins comprise at least one isoparaffin selected from the group consisting of isobutane, isopentane, and mixtures thereof.

7. The process according to claim 1, wherein the ionic liquid catalyst is selected from the group consisting of:
    a chloroaluminate ionic liquid catalyst comprising a hydrocarbyl substituted pyridinium halide or a hydrocarbyl substituted imidazolium halide of the general formulas A and B, respectively;
    a chloroaluminate ionic liquid catalyst comprising an alkyl substituted pyridinium halide or an alkyl substituted imidazolium halide of the general formulas A and B, respectively;

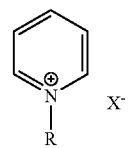

(A)

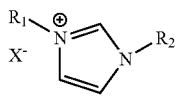

and mixtures thereof,
where R=H, methyl, ethyl, propyl, butyl, pentyl or hexyl group and X is a haloaluminate and $R_1$ and $R_2$=H, methyl, ethyl, propyl, butyl, pentyl, or hexyl group and where $R_1$ and $R_2$ may or may not be the same.

8. The process according to claim 7, wherein the ionic liquid catalyst is selected from the group consisting of 1-butyl-4-methyl-pyridinium chloroaluminate (BMP), 1-butyl-pyridinium chloroaluminate (BP), 1-butyl-3-methyl-imidazolium chloroaluminate (BMIM), 1-H-pyridinium chloroaluminate (HP), and N-butylpyridinium chloroaluminate.

9. The process according to claim 7, wherein the catalyst further comprises an HCl co-catalyst.

10. The process according to claim 1, wherein the alkylation conditions include a catalyst volume in the reactor of from 5 vol % to 50 vol %, a temperature of from −10° C. to 100° C., a pressure of from 300 kPa to 2500 kPa, an initial paraffin to olefin molar ratio of from 2 to 10 and a residence time of 1 minute to 1 hour.

11. The process of claim 1, wherein the feed streams are fed into the reactor through nozzles.

12. A process for the production of low volatility, high quality gasoline blending components comprising:
(a) providing an isoparaffin feed stream comprising isoparaffins;
(b) providing an olefin feed stream comprising olefins;
(c) providing a catalyst stream comprising an ionic liquid catalyst;
(d) splitting the isoparaffin feed stream and the olefin feed stream into multiple isoparaffin feed streams and olefin feed streams;
(e) feeding the multiple isoparaffin feed streams and olefin feed streams into a vertical downflow reactor at different feed sites along the length of the reactor for each isoparaffin and olefin feed stream while also feeding the catalyst feed stream into the reactor to contact all the feed streams under alkylation conditions to provide a product comprising the low volatility, high quality gasoline blending components wherein the isoparaffin/olefin ratio increases along the length of the reactor; and
(f) isolating the low volatility, high quality gasoline blending components from the product.

13. The process according to claim 12, wherein the isoparaffin and olefin streams are fed into the reactor in at least 3 different sites.

14. The process according to claim 12, wherein:
the olefins comprise at least one olefin selected from the group consisting of ethylene, propylene, butene, pentene, and mixtures thereof;
the isoparaffins comprise at least one isoparaffin selected from the group consisting of isobutane, isopentane, and mixtures thereof; and
the catalyst is selected from the group consisting of 1-butyl-4-methyl-pyridinium chloroaluminate (BMP), 1-butyl-pyridinium chloroaluminate (BP), 1-butyl-3-methyl-imidazolium chloroaluminate (BMIM), 1-H-pyridinium chloroaluminate (HP), and N-butylpyridinium chloroaluminate.

15. The process according to claim 12, further comprising recycling unreacted isoparaffin and catalyst to the reactor.

16. The process according to claim 1, further comprising recycling unreacted isoparaffin and catalyst to the reactor.

* * * * *